United States Patent [19]
Braxton et al.

[11] Patent Number: 6,033,848
[45] Date of Patent: Mar. 7, 2000

[54] HUMAN ICE HOMOLOG

[75] Inventors: Scott Michael Braxton, San Mateo; Dinh Diep, San Francisco; Jeffrey J. Seilhamer, Los Altos Hills, all of Calif.

[73] Assignee: Incyte Pharmaceuticals, Inc., Palo Alto, Calif.

[21] Appl. No.: 08/522,813

[22] Filed: Aug. 1, 1995

[51] Int. Cl.$^7$ .............................. C12Q 1/68; C07H 21/04; C12N 9/00; C12P 21/02

[52] U.S. Cl. .............................. 435/6; 435/69.1; 435/183; 435/320.1; 536/23.1; 536/23.2; 536/24.1

[58] Field of Search .............................. 435/69.1, 320.1, 435/6, 183; 536/23.1, 24.1, 23.2

[56] References Cited

U.S. PATENT DOCUMENTS

| | | | |
|---|---|---|---|
| 5,654,146 | 8/1997 | Braxton et al. | 435/6 |
| 5,808,001 | 9/1998 | Braxton et al. | 530/387.1 |
| 5,856,169 | 1/1999 | Litwack et al. | 435/252.3 |

OTHER PUBLICATIONS

Kamens et al. Identification and Characterization of ICH–2, a Novel Member of the Interleukin 1B–converting Enzyme Family of Cysteine Proteases. J. Biol. Chem. 270 (25): 15250–15256, Jun. 23, 1995.

Munday et al. Molecular Cloning and Pro–Apoptotic Activity of ICEreIII and ICEreIIII, Members of the ICE/CED–3 Family of Cysteine Proteases. J. Biol. Chem. 270 (26: 15870–15876, Jun. 30, 1995.

Ayala et al., "IL–1β–Converting Enzyme Is Present in Monocytic Cells as an Inactive 45–kDa Precursor," *J. Immunol.* 53:2592–2599 (1994).

Li et al., "Mice Deficient in IL–1β–Converting Enzyme Are Defective in Production of Mature IL–1β and Resistant to Endotoxic Shock," *Cell* 80:401–411 (Feb. 10, 1995).

Howard et al., "IL–1–Converting Enzyme Requires Aspartic Acid Residues for Processing of the IL–1β Precursor at Two Distinct Sites and Does Not Cleave 31–kDa ILα," *J. Immunol.* 147 (9):2964–2969 (Nov. 1, 1991).

Carruth et al., "Involvement of a Calpain–like Protease in the Processing of the Murine Interleukin 1α Precursor," *J. Biol. Chem.* 266(9):12162–12167 (1991).

Miura et al., "Induction of Apoptosis in Fibroblasts by IL–1β–Converting Enzyme, a Mammalian Homolog of the C. elegans Cell Death Gene ced–3," *Cell* 75:653–660 (Nov. 19, 1993).

Walker et al., "Crystal Structure of the Cysteine Protease Interleukin–1β–Converting Dnzyme: A(p20/p10)$_2$ Homodimer," *Cell* 75:641–652 (Nov. 19, 1993).

Yuan et al., "The C. elegans Cell Death Gene ced–3 Encodes a Protein Similar to Mammalian Interleukin–1β–Converting Enzyme," *Cell* 75:641–652 (Nov. 19, 1993).

Dinarello et al., "Mechanisms of Disease, The Role of Interleukin–1 in Disease," *N. Engl. J. Med.* 328(2):106–113 (Jan. 14, 1993).

Romaris et al., "Differential effect of transforming growth factor β on proteoglycan synthesis in human embryonic lung fibroblasts," *Biochem Biophys. Acta.* 1093:229–233 (1991).

McCusker et al., "Mechanisms of Respiratory Tissue Injury from Cigarette Smoking," *Amer. J. Med.* 93(supp 1A):18S–21S (Jul. 15, 1992).

*Primary Examiner*—Nancy Degen
*Attorney, Agent, or Firm*—Incyte Pharmaceuticals, Inc.

[57] ABSTRACT

The present invention provides a polynucleotide (icel) which identifies and encodes a human ice homolog (ICEL) expressed in lung cells and tissues. The present invention also provides for antisense molecules and oligomers designed from the nucleotide sequence or its antisense. The invention further provides genetically engineered expression vectors and host cells for the production of purified ICEL peptide, antibodies capable of binding to ICEL, inhibitors which bind to ICEL and pharmaceutical compositions based on ICEL specific antibodies or inhibitors. The invention specifically provides for diagnostic assays which identify a disorder or disease with altered icel expression which allows identification and monitoring of hospital patients. These assays utilize icel encoding or controlling nucleic acid sequences, fragments or oligomers thereof, or antibodies specific for the peptide.

9 Claims, 6 Drawing Sheets

```
                9              18             27             36             45             54
5' ATT CGG TAC GAG CTG AGG TGG ATG TCA GCC TCC GTT TAC ACG CTG CCT GCT GGA
   I   R   Y   E   L   R   W   M   S   A   S   V   Y   T   L   P   A   G 63             72             81             90             99            108
   GCT GCA CTT CCT CAT GAT CCG GCA GAA AAG TAC AAA ATG GAC CAC AGG AGG AGA
   A   A   L   P   H   D   P   A   E   K   Y   K   M   D   H   R   R   R 117            126            135            144            153            162
   GGA ATT GCT TTA ATC TTC AAT CAT GAG AGG TTC TTT TGG CAC TTA ACA CTG CCA
   G   I   A   L   I   F   N   H   E   R   F   F   W   H   L   T   L   P 171            180            189            198            207            216
   GAA AGG CGG GGC ACC TGC GCA GAT AGA GAC AAT CTT ACC CGC AGG TTT TCA GAT
   E   R   R   G   T   C   A   D   R   D   N   L   T   R   R   F   S   D 225            234            243            252            261            270
   CTA GGA TTT GAA GTG AAA TGC TTT TAT GAT CTT AAA GCA GAA GAA CTA CTG CTC
   L   G   F   E   V   K   C   F   Y   D   L   K   A   E   E   L   L   L 279            288            297            306            315            324
   AAA ATT CAT GAG GTG TCA ACT GTT AGC CAC GCA GAT GCC GAT TGC TTT GTG TGT
   K   I   H   E   V   S   T   V   S   H   A   D   A   D   C   F   V   C 333            342            351            360            369            378
   GTC TTC CTG AGC CAT GGC GAA GGC AAT CAC ATT TAT GCA TAT GAT GCT AAA ATC
   V   F   L   S   H   G   E   G   N   H   I   Y   A   Y   D   A   K   I 387            396            405            414            423            432
   GAA ATT CAG ACA TTA TCT GGC TCG TTC AAA GGA GAC AAG TGT CAC AGC CTG GTT
   E   I   Q   T   L   S   G   S   F   K   G   D   K   C   H   S   L   V 441            450            459            468            477            486
   GGA AAA CCC AAG ATA TTT ATC ATT CAG GCA TGT CGG GGA AAC CAG CAC GAT GTG
   G   K   P   K   I   F   I   I   Q   A   C   R   G   N   Q   H   D   V 495            504            513            522            531            540
   CCA GTC ATT CCT TTG GAT GTA GTA GAT AAT CAG ACA GAG AAG TTG GAC ACC AAC
   P   V   I   P   L   D   V   V   D   N   Q   T   E   K   L   D   T   N 549            558            567            576            585            594
   ATA ACT GAG GTG GAT GCA GCC TCC GTT TAC ACG CTG CCT GTT GGA GCT GAC TTC
   I   T   E   V   D   A   A   S   V   Y   T   L   P   V   G   A   D   F 603            612            621            630            639            648
   CTC ATG TGT TAC TCT GTT GCA GAA GGA TAT TAT TCT CAC CGG GAA ACT GTG AAC
   L   M   C   Y   S   V   A   E   G   Y   Y   S   H   R   E   T   V   N
```

FIGURE 1A

```
         657              666              675              684              693              702
GGT TCA TGG TAC ATT CAA GAT TTG TGT GAG ATG TTG GGA AAA TAT GGC TCC TCC
 G   S   W   Y   I   Q   D   L   C   E   M   L   G   K   Y   G   S   S 711              720              729              738              747              756
TTA GAG TTC ACA GAA CTC CTC ACA CTG GTG AAC AGG AAA GTT TCT CAG CGC CGA
 L   E   F   T   E   L   L   T   L   V   N   R   K   V   S   Q   R   R 765              774              783              792              801              810
GTG GAC TTT GGC AAA GAC CCA AGT GCA ATT GGA AAG AAG CAG GTT CCC TGT TTG
 V   D   F   G   K   D   P   S   A   I   G   K   K   Q   V   P   C   L 819              828              837              846              855              864
GGC TCA ATG CTA ACT AAA AAG CTG CAT TTC TTT CCA AAA TCT AAT TAA TTA ATA
 G   S   M   L   T   K   K   L   H   F   F   P   K   S   N   *   L   I 873              882              891              900              909              918
GAG GCT ATC TAA TTT CAC ACT CTG TAT TGA AAA TGG CTT TCT CAG CCA GGC GTG
 E   A   I   *   F   H   T   L   Y   *   K   W   L   S   Q   P   G   V 927              936              945              954              963              972
GTT ACT CAC ACC TGT AAT CCC AGC ACT TTG GGA GTC CAA GGT GGG CGG ATC ACC
 V   T   H   T   C   N   P   S   T   L   G   V   Q   G   G   R   I   T 981              990              999             1008             1017             1026
TGA GGT CGG GAG TTC GAG ACC AGC CTG ACC AAC ATG GAG GAA GCC CCG TCT CTT
 *   G   R   E   F   E   T   S   L   T   N   M   E   E   A   P   S   L 1035             1044             1053             1062             1071             1080
ACT AAA AAT GCA AAA AAA AAT TTA GCT AGG GAT GGG GGC ATG CCT GCA ATC CCA
 T   K   N   A   K   K   N   L   A   R   D   G   G   M   P   A   I   P 1089             1098             1107             1116             1125             1134
GCT ACT TGG AAG GCT GAG GGA GGA GAT CAC TTG ACC CAG GAG GTG GAG GTT GNG
 A   T   W   K   A   E   G   G   D   H   L   T   Q   E   V   E   V   X 1143             1152             1161             1170             1179             1188
GTG AAC CGA TAT TGC ACC ANT GNA CTC CAG CCT GGG NAA NGA GTG AAC TCC CNC
 V   N   R   Y   C   T   X   X   L   Q   P   G   X   X   V   N   S   X

1197
TCA AAA AAA AAA GAA A 3'
 S   K   K   K   E
```

FIGURE 1B

```
        M S A S V N S V D A G A A L N L D P K I I H G S E S M D S G  Majority
                        10                  20                  30
 1      M S A S V Y T L P A G A A L P H D P - - - - - - - - - - - -  124985 (Ice homolog)
 1      M E N T E N S V D S K S I K N L E P K I I H G S E S M D S G  Human cysteine protease I S L A E S Y K M D H R E R G L A L I I N N E N F H K S L G  Majority
                        40                  50                  60
19      - - - A E K Y K M D H R R R G I - L I F H H E F F F H L T    124985 (Ice homolog)
31      I S L D N S Y K M D Y P E M G L C I I I N K N F H K S T G    Human cysteine protease L T S R S G T D A D A A N L T E T F S D L G F E V K N K N D  Majority
                        70                  80                  90
46      L P E R R G T C A D R D N L T R R F S D L G F E V K C F Y D  124985 (Ice homolog)
61      M T S R S G T D V D A A N L R E T F R N I K Y E V R N K N D  Human cysteine protease L T A E E L V L L I H D V S T V S H A D A S S F V C V L L S  Majority
                        100                 110                 120
76      L K A E E L L L K I H E V S T V S H A D A D C F V C V F L S  124985 (Ice homolog)
91      L T R E E I V E L M R D V S K E D H S K R S S F V C V L L S  Human cysteine protease H G E G G I I F G T D G K V D L Q T L S G S F K G D K C H S  Majority
                        130                 140                 150
106     H G E G N H I Y A Y D A K I E I Q T L S G S F K G D K C H S  124985 (Ice homolog)
121     H G E E G I I F G T N G P V D L K K I T N F F R G D R C R S  Human cysteine protease L V G K P K L F I I Q A C R G T E L D V G V I P L D V V D N  Majority
                        160                 170                 180
136     L V G K P K I F I I Q A C R G H Q H D V P V I P L D V V D N  124985 (Ice homolog)
151     L T G K P K L F I I Q A C R G T E L D C G I - - - - - - - -  Human cysteine protease Q T E K L D T D I G V V D A A A V H T L P V G A D F L Y A Y  Majority
                        190                 200                 210
166     Q T E K L D T H I T E V D A A S V T L P V G A D F L H T      124985 (Ice homolog)
173     - - - - - E T D S G V D D D M A C H K I P D A D F L Y A      Human cysteine protease
```

FIGURE 2A

```
            S V A E G Y Y S H R E S V D G S W F I Q S L C A M L G Q Y G  Majority
                         220                 230                 240
     196.  S V A E G Y Y S H R E T V N G S   Y I Q D L C E H L G K Y G  124985 (Ice homolog)
     198.  S T A P G Y Y S W R N S K D G S   F I   S L C A H L K Q Y A  Human cysteine protease S S L E F T E L L T L V N R K V A T E R V S F G K D A S A I  Majority
                         250                 260                 270
     226.  S S L E F T E L L T L V N R K V S Q R R V D F G K D P S A I  124985 (Ice homolog)
     228.  D K L E F M H I L T R V N R K V A T E F E S F S F D A T F H  Human cysteine protease G K K Q V P C L G S M L T K E L H F F P K S N          Majority
                         280                 290
     256.  G K K Q V P C L G S M L T K K L H F F P K S H          124985 (Ice homolog)
     258.  A K K Q I P C I V S M L T K E L Y F Y - - - H          Human cysteine protease
```

Decoration 'Decoration #1': Shade (with solid black) residues that match 124985

FIGURE 2B ive form. (Ayala,

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 1183 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Lung
        (B) CLONE: 124985

(xi) SEQUENCE DESCRIPTION: SEQ ID NO:1:

```
ATGTCAGCCT CCGTTTACAC GCTGCCTGCT GGAGCTGCAC TTCCTCATGA TCCGGCAGAA      60

AAGTACAAAA TGGACCACAG GAGGAGAGGA ATTGCTTTAA TCTTCAATCA TGAGAGGTTC     120

TTTTGGCACT TAACACTGCC AGAAAGGCGG GGCACCTGCG CAGATAGAGA CAATCTTACC     180

CGCAGGTTTT CAGATCTAGG ATTTGAAGTG AAATGCTTTT ATGATCTTAA AGCAGAAGAA     240

CTACTGCTCA AAATTCATGA GGTGTCAACT GTTAGCCACG CAGATGCCGA TTGCTTTGTG     300

TGTGTCTTCC TGAGCCATGG CGAAGGCAAT CACATTTATG CATATGATGC TAAAATCGAA     360

ATTCAGACAT TATCTGGCTC GTTCAAAGGA GACAAGTGTC ACAGCCTGGT TGGAAAACCC     420

AAGATATTTA TCATTCAGGC ATGTCGGGGA AACCAGCACG ATGTGCCAGT CATTCCTTTG     480

GATGTAGTAG ATAATCAGAC AGAGAAGTTG GACACCAACA TAACTGAGGT GGATGCAGCC     540
```

```
TCCGTTTACA CGCTGCCTGT TGGAGCTGAC TTCCTCATGT GTTACTCTGT TGCAGAAGGA      600

TATTATTCTC ACCGGGAAAC TGTGAACGGT TCATGGTACA TTCAAGATTT GTGTGAGATG      660

TTGGGAAAAT ATGGCTCCTC CTTAGAGTTC ACAGAACTCC TCACACTGGT GAACAGGAAA      720

GTTTCTCAGC GCCGAGTGGA CTTTGGCAAA GACCCAAGTG CAATTGGAAA GAAGCAGGTT      780

CCCTGTTTGG GCTCAATGCT AACTAAAAAG CTGCATTTCT TTCCAAAATC TAATTAATTA      840

ATAGAGGCTA TCTAATTTCA CACTCTGTAT TGAAAATGGC TTTCTCAGCC AGGCGTGGTT      900

ACTCACACCT GTAATCCCAG CACTTTGGGA GTCCAAGGTG GGCGGATCAC CTGAGGTCGG      960

GAGTTCGAGA CCAGCCTGAC CAACATGGAG GAAGCCCCGT CTCTTACTAA AAATGCAAAA     1020

AAAAATTTAG CTAGGGATGG GGGCATGCCT GCAATCCCAG CTACTTGGAA GGCTGAGGGA     1080

GGAGATCACT TGACCCAGGA GGTGGAGGTT GNGGTGAACC GATATTGCAC CANTGNACTC     1140

CAGCCTGGGN AANGAGTGAA CTCCCGCTCA AAAAAAAAAA AAA                       1183

(2) INFORMATION FOR SEQ ID NO:2:

(i) SEQUENCE CHARACTERISTICS:
         (A) LENGTH: 227 base pairs
         (B) TYPE: nucleic acid
         (C) STRANDEDNESS: single
         (D) TOPOLOGY: linear (ii) MOLECULE TYPE: cDNA (vii) IMMEDIATE SOURCE:
         (A) LIBRARY: Kidney
         (B) CLONE: 194094

(xi) SEQUENCE DESCRIPTION: SEQ ID NO:2:

GAGAAGTGAG GCTGATGTCT GTGAAGTTGG GTCAGNGTAC TCGAAATTCC CCATGTGGTT       60

GGAGAACTTA GGCATTGAAA GTAATTTTTT GGCCAGGCGT GGTGGCTCAC ACCTGTAATC      120

CCAGCACTTT NGGAGGCCAA GTTGGGCGGN TCACCTGAGG TCGGGAGTTC GAGACCAGAC      180

TGNCCAACAT GAAGAAATCC CATNTCTACT AAAAATACAA AATTAGG                    227

(2) INFORMATION FOR SEQ ID NO:3:

(i) SEQUENCE CHARACTERISTICS:
         (A) LENGTH: 390 base pairs
         (B) TYPE: nucleic acid
         (C) STRANDEDNESS: single
         (D) TOPOLOGY: linear (ii) MOLECULE TYPE: cDNA (vii) IMMEDIATE SOURCE:
         (A) LIBRARY: U937
         (B) CLONE: 239

(xi) SEQUENCE DESCRIPTION: SEQ ID NO:3:

CCAGCACGAT GTNCAGTCAT TNCTTTGGAT GTAGTAGATA ATCAGACAGA GAAGTTGGAC       60

ACCAACATAA CTGAGGTGGT TGCAGCCTCC GTTTACACGC TGCCTGTTGG AGCTGACTTC      120

CTCATGTGTT ACTCTGTTGC AGAAGGATAT TATTCTCACC GGGAAACTGT GAACGGTTCA      180

TGGTACATTC AAGATTTGTG TGAGATGTTG GGAAAAATAT GGCTCCTCCT TAGAGTTCAC      240

AGAACTTCTC ACACTGGTGA ACAGGAAAGT TTCTNAGCGC CGAGTGGACT TTTGCAAGNC      300

CCAAAGNGCA ATTTNGAAAN GNAAGCANGT TTCCCTGTTT TTGCCTCAAA TGCNTAANCT      360

AAAAAAGGCT GCATTNNNTT TCNAAAATCT                                       390

(2) INFORMATION FOR SEQ ID NO:4:
```

```
    (i) SEQUENCE CHARACTERISTICS:
        (A) LENGTH: 278 amino acids
        (B) TYPE: amino acid
        (D) TOPOLOGY: linear (ii) MOLECULE TYPE: protein (xi) SEQUENCE DESCRIPTION: SEQ ID NO:4:

Met Ser Ala Ser Val Tyr Thr Leu Pro Ala Gly Ala Ala Leu Pro His
1               5                   10                  15

Asp Pro Ala Glu Lys Tyr Lys Met Asp His Arg Arg Arg Gly Ile Ala
                20                  25                  30

Leu Ile Phe Asn His Glu Arg Phe Phe Trp His Leu Thr Leu Pro Glu
            35                  40                  45

Arg Arg Gly Thr Cys Ala Asp Arg Asp Asn Leu Thr Arg Arg Phe Ser
        50                  55                  60

Asp Leu Gly Phe Glu Val Lys Cys Phe Tyr Asp Leu Lys Ala Glu Glu
65                  70                  75                  80

Leu Leu Leu Lys Ile His Glu Val Ser Thr Val Ser His Ala Asp Ala
                85                  90                  95

Asp Cys Phe Val Cys Val Phe Leu Ser His Gly Glu Gly Asn His Ile
                100                 105                 110

Tyr Ala Tyr Asp Ala Lys Ile Glu Ile Gln Thr Leu Ser Gly Ser Phe
            115                 120                 125

Lys Gly Asp Lys Cys His Ser Leu Val Gly Lys Pro Lys Ile Phe Ile
130                 135                 140

Ile Gln Ala Cys Arg Gly Asn Gln His Asp Val Pro Val Ile Pro Leu
145                 150                 155                 160

Asp Val Val Asp Asn Gln Thr Glu Lys Leu Asp Thr Asn Ile Thr Glu
                165                 170                 175

Val Asp Ala Ala Ser Val Tyr Thr Leu Pro Val Gly Ala Asp Phe Leu
            180                 185                 190

Met Cys Tyr Ser Val Ala Glu Gly Tyr Tyr Ser His Arg Glu Thr Val
        195                 200                 205

Asn Gly Ser Trp Tyr Ile Gln Asp Leu Cys Glu Met Leu Gly Lys Tyr
    210                 215                 220

Gly Ser Ser Leu Glu Phe Thr Glu Leu Leu Thr Leu Val Asn Arg Lys
225                 230                 235                 240

Val Ser Gln Arg Arg Val Asp Phe Gly Lys Asp Pro Ser Ala Ile Gly
                245                 250                 255

Lys Lys Gln Val Pro Cys Leu Gly Ser Met Leu Thr Lys Lys Leu His
            260                 265                 270

Phe Phe Pro Lys Ser Asn
            275         278
```

HUMAN ICE HOMOLOG

FIELD OF THE INVENTION

The present invention is in the field of molecular biology; more particularly, the resent invention describes nucleic acid and amino acid sequences of a novel interleukin-1 converting enzyme homolog from lung cells.

BACKGROUND OF THE INVENTION

To understand the interleukin 1 converting enzyme (ICE), it is helpful to first examine the role of interleukin-1 (IL-1), its enzymatic substrate. IL-1 facilitates host natural immunity, predominantly those aspects related to the initiation of inflammatory reactions that protect the body against bacterial infection. (Ayala et al. (1994) J Immunol 53: 2592–2599). At low concentrations in the bloodstream, IL-1 mediates local inflammation by inducing the synthesis of other cytokines, such as IL-6 and IL-8, and the synthesis of proteins that mediate leukocyte adhesion, and prostaglandin production. (Abbas et al. (1994) *Cellular and Molecular Immunology*, W B Saunders Company). At intermediate concentrations in the bloodstream, IL-1 may induce fever, the synthesis of acute plasma proteins by the liver, and metabolic wasting, cachexia (Abbas, supra). At even higher concentrations, IL-1 has been implicated in tissue destruction observed in numerous inflammation-related diseases, including rheumatoid arthritis, septic shock, inflammatory bowel disease and insulin-dependent diabetes mellitus. (Li et al. (1995) Cell 80:401–411).

IL-1 activity results from the expression and release of two gene products, IL-1α and IL-1β, predominantly from activated monocytes. (Howard et al. (1991) J Immunology 147:2964–2969). Both gene products are initially synthesized as inactive precursors of about 31 kD in monocytes. Pre-IL-1β is cleaved to an active 17 kD form by the IL-1β-converting enzyme (ICE) before release from activated monocytes. On the other hand, pre-IL-1α is likely cleaved to an active 17 kD form by a calpain-like, IL-1α-converting enzyme prior to release. (Carruth et al. (1991) J Biol Chem 266:12162–12167). Additionally, ICE has been implicated in the release of IL-1α from activated monocytes but the mechanism is not understood (Li, supra).

The IL-1β gene product is the predominant form of IL-1 that is present at high concentrations in the bloodstream during inflammatory diseases, such as rheumatoid arthritis, septic shock, inflammatory bowel disease, and insulin-dependent diabetes mellitus (Li, supra). Since the cleavage of pre-IL-1β by ICE is coupled to IL-1β release and to increased IL-1 activity in the bloodstream, ICE activity may be higher in these pathological conditions.

The importance of regulating ICE activity to modulate the IL-1β concentration to affect the host immune response has recently been confirmed: the crmA gene product of cowpox virus prevents the proteolytic activation of IL-1β and inhibits the host inflammatory response. Cowpox virus containing a deleted crmA gene is unable to suppress the inflammatory response, resulting in a reduction of virus-infected cells and less damage to the host. (Miura et al. (1993) Cell 75: 653–660).

ICE is a novel cysteine protease that is known specifically to cleave inactive IL-1β precursor to its active form. (Ayala, supra). This protease recognizes the sequence Asp-X, where X is preferably a small hydrophobic amino acid residue, and cleaves the bond between Asp and X. However, many Asp-X bonds are not recognized by ICE suggesting that flanking sequences are also required for recognition and cleavage. In the case of IL-1β, ICE cleaves the precursor to form active IL-1β at two sequence-specific bonds: the bond between residues Asp-27 and Gly-28 and the bond between residues Asp-116 and Ala-117.

ICE itself is synthesized and maintained in cells as an inactive 45 kD precursor which is processed into the active ICE consisting of 20- and 10-kD subunits, p20 and p10. (Ayala, supra). The 45 kD precursor which is cleaved into four different fragments: a 13 kD precursor domain, the p20, a 2 kD spacer, and the p10. Since all these polypeptide fragments are flanked by Asp-X residues in the intact 45 kD precursor, it is possible that the ICE precursor is activated autocatalytically. (Ayala, supra).

The three dimensional structure of ICE has been determined from crystallographic studies. (Walker et al. (1994) Cell 78:343–352). First, it is apparent that the active form of ICE is a homodimer of catalytic domains, each of which consists of p20 and p10 subunits. Second, although the active site cysteine residue is located on p20, both p20 and p10 are essential for activity. p20 and p10 structures are intertwined so as to create a unique 6-stranded, β-sheet core flanked on either side by α helices. The first 4 β strands ,are contributed by p20, while the remaining 2 β strands are contributed by p10.

The ICE gene from various sources has been sequenced and possesses homology (29% homology overall) to the product of a gene with a possible role in apoptosis: the *Caenorhabditis elegans* gene ced-3. (Yuan et al. (1993) Cell 75: 641–652). Additionally, the ICE gene contains a sequence region, spanning residues 166 to 287 of the human ICE gene, which shares a 43% homology with ced-3. It is not known whether ced-3 acts as a cysteine protease but it contains the purported catalytic residues that are located at the ICE active site ($Cys_{285}$ and $His_{237}$). The amino acid pentapeptide Glu—Ala—Cys—Arg—Gly (QACRG), containing the active site cysteine, is the longest oligopeptide conserved among ICE from mice and humans and CED-3 from three different nematodes. Additionally, ced-3 contains the same four residues whose side chains are implicated in binding the aspartate carboxylate group of the substrate at the catalytic site, $Arg_{179}$, $Gln_{283}$, $Ser_{347}$, and $Arg_{341}$ (Yuan, supra).

Inhibition with the ICE-specific inhibitor crmA blocks TNF- and FAS-induced apoptosis. Therefore, ICE or a homolog of the molecule is believed to be involved in TNF-and FAS-induced apoptosis.

Additionally, ICE possesses a degree of homology to a gene product with a possible role in embryogenesis: the mammalian gene Nedd-2/Ich-1 is expressed during embryonic brain development and is down-regulated in the adult brain. (Yuan, supra). Nedd-2, ced-3, and ICE gene products are about 27% homologous with the carboxyterminus of CED-3 and p10 possessing the highest degree of homology to Nedd-2. The Nedd-2 gene product does not contain the highly conserved QACRG pentapeptide so Nedd-2 probably is not a cysteine protease.

To confirm ICE's role in inflammation-related diseases by controlling the levels of active IL-1β, ICE-deficient knock-out mice were created (Li, supra). These genetically-engineered mice were normal physiologically but lacked the ability to process precursor IL-1β to its active form when monocytes were activated with microbial products, such as lipopolysaccharide (LPS). Additionally, the production of IL-1α was decreased, and the level of other cytokines, tumor necrosis factor (TNF) and IL-6, involved in inflammatory responses to microbial products was somewhat reduced.

These mice were resistant to the lethal effects of septic shock when exposed to LPS (Li, supra). Therefore, inhibiting ICE activity to lower the concentration of IL-1β in the bloodstream may be a method of treating inflammation-related diseases. ICE also may help identify patients who are susceptible to these diseases.

Since ICE shares sequence homology to ced-3 and overexpression of ICE appears to induce apoptosis, the ICE-deficient mice studies were important because the mice seemed normal in terms of their development. If ICE itself played a strong role in apoptosis during development, the ICE-deficient mice should have had gross abnormalities in brain, gut, lymphoid and brain tissues, and have autoimmune diseases (Li, supra). This implies that other ICE-like proteins are involved in these aspects. However, ICE may perform functions other than IL-1β precursor cleavage. ICE mRNA has been detected in a greater variety of tissues than IL-1β mRNA has (Miura, supra).

ICE has attracted interest as a target for novel anti-inflammatory drugs, because the cytokine which it activates, IL-1β, is proinflammatory and has been implicated in the pathophysiology of various diseases, including rheumatoid arthritis, septic shock, inflammatory bowel disease and insulin-dependent diabetes mellitus (Dinarello and Wolff (1993) N Engl J Med 328:106–13). The provision of a new ICE gene and polypeptide will further drug research in screening for and designing more effective and more specific inhibitors to this pro-inflammatory substance. The ICE molecule which is the subject of this patent application was identified among the sequences of a cDNA library made from human lung. A short description of the organ and its cells follows.

The Lung

The respiratory system is composed of 1) a ventilation mechanism, 2) a conduction passageway comprising the nasal cavity, nasopharynx, larynx, trachea, bronchi, bronchioles, and terminal bronchioles which cleans, moistens, and warms incoming air, and 3) a respiratory portion of the lungs comprising the respiratory bronchioles, alveolar ducts, and alveoli where gas exchange takes place.

Respiratory Mucosa

Beginning in the nasal cavity and extending through the larger bronchioles, air passageways are coated with a viscoelastic sheet produced by mucous and serous cells located in the surface epithelium and underlying submucosal glands. The surface epithelium is pseudostratified and typically contains mucus-producing goblet cells, ciliated columnar cells, brush cells, basal cells, and small granule cells.

Mucins are large glycoproteins which form the structural components of the viscoelastic layer. They are synthesized in intracellular granules in surface goblet cells and the mucous cells of the submucosa glands. The release of mucin is accompanied by swelling and gel formation similar to that occurring in the intestinal tract. Water and ions primarily from ciliated cells accomplish the hydration.

Serous cells, which comprise the majority of cells in the submucosal glands, make and secrete immunoglobulin A (IgA). Dense granules in the serous cells contain lysozyme and antiproteases, which inactivate destructive bacterial enzymes. The antiproteases also destroy proteases released by neutrophils before they can cause the secondary damage common to pulmonary disease. Within serous cell granules the positively charged secretory proteins are bound to negatively charged sulfated proteoglycans. Opposite-charge packing, common to many granules, is a mechanism that concentrates contents by reducing osmotic activity to exclude water. In addition to their structural role within the granule, proteoglycans released with secretory proteins during exocytosis are incorporated into the mucin layer and may make important contributions to its physical substructure.

The blanket-like secretion covering the epithelium is continually moved towards the pharynx by the coordinated activity of the cilia which project from up to 90% of the surface epithelial cells. These cilia move in an undulating wave in a low-viscosity layer under the viscoelastic sheet. Organisms and particles trapped within the mucous layer are carried to the pharynx, where they are swallowed or expectorated. This "clearance" of the airway is the primary factor preventing respiratory damage and infection. In respiratory diseases such as asthma, chronic bronchitis, and cystic fibrosis there is a hypersecretion of mucus and hyperplasia of goblet cells. Excess mucus obstructs the airway, halting the clearing feature; if bacteria and viruses accumulate and overwhelm cellular defense, infection results.

Bronchioles are located between the larger airways which contain cartilage and extensive submucosal glands and the delicate alveoli where gas exchange occurs. The alveoli have a high proportion of circularly arranged smooth muscle and are lined with epithelial cells. In the terminal bronchioles, the epithelium is cuboidal and consists of ciliated and nonciliated cells. The ciliated cells move secretions and trapped airborne particles towards the pharynx. The nonciliated cells are unique to bronchioles and their major function is secretion of the material lining the bronchiolar lumen. This material contains proteins important in defense (eg, lysozyme and antibodies) and in breaking up the mucus produced in the upper airway. Typically, nonciliated cells have an apical region of densely packed granules and large mitochondria and a basal portion which contains the nucleus, rough endoplasmic reticulum (ER), and patches of glycogen. The cells' smooth ER may function to detoxify a variety of compounds, and the granules may have lysosomal function for recycling secretions.

Of all the respiratory passageways, the bronchiole is occluded most easily. Because of the small size of the bronchiolar lumen, factors associated with disease, such as spasmodic contraction of smooth muscles (as in asthma) or abnormal production of mucus (as in chronic bronchitis due to smoking) can close bronchioles and reduce airflow enough to be life threatening. During an allergic response, parasympathetic nerves that innervate the smooth muscle of the bronchioles release acetylcholine, a bronchoconstrictor. Bronchioles are also particularly sensitive to mediators, such as leukotrienes from mast cells.

Gas exchange occurs in the over 300 million bubble-like alveoli at the end of the respiratory passageways. Type I alveolar cells, which are simple squamous cells, and Type II alveolar cells, which are intermittent cuboidal secretory cells, line the alveoli and are continuous with the cuboidal epithelium lining the terminal bronchioles. A network of pulmonary capillaries surround each alveolus. Oxygen and carbon dioxide diffuse across the cell layers of the alveoli which form the blood-air barrier into the capillary blood and carbon dioxide diffuses in the opposite direction. Carbonic anhydrase present in red blood cells in the capillaries liberates $CO_2$ from $H_2CO_3$.

The interalveolar septum is composed of five main cell types: capillary endothelial cells (30%); Type I alveolar cells (8%); Type II alveolar cells (16%); interstitial cells, including fibroblasts and mast cells (36%); and alveolar macrophages (10%). Macrophages are present within the air space and in the interstitial tissue of the alveolar septa. When activated by airborne irritants, macrophages recruit blood cells such as lymphocytes to aid in their defensive efforts. Eventually, as the disease state progresses, blood cells can enter the air space to join the macrophages, resulting in congestive heart failure.

The primary role of the interstitial fibroblast of the lung is the maintenance of the integrity of the alveolar compartment by its production of collagens, predominantly Types I and III collagen, elastin fibers, and other matrix components, including fibronectin and proteoglycans (PGs). Human lung fibroblasts secrete the two small chondroitin/dermatan sulfate PGs, PG-I (biglycan, 300 kD) and, in larger proportion, PG-II (decorin, 130 kD). Transforming growth factor-beta (TGF-β), which acts as a growth inhibitor, selectively induces the expression of PG-I, but not PG-II. PG-I and PG-II may act as mediators of the growth inhibition caused by TGF-β (Romaris et al (1991) Biochim Biophys Acta 1093:229–33).

Collagen supports the septum, and elastin fibers accommodate the stretching associated with the respiration. Fibroblasts also synthesize a variety of enzymes, including collagenase, and products that may modulate the function of other cells. These include chemotactic factors, prostaglandins, tissue plasminogen activator (tPA), components of the complement system, and superoxide dismutase. During early lung development and under the regulation of glucocorticoids, fibroblasts produce a pneumocyte factor that stimulates the synthesis of surfactant by alveolar type 2 cells. In the event of injury to the septum, fibroblasts divide and secrete more collagen for repair. Chronic insult leads to the overproduction of collagen and to scarring which interferes with gas exchange.

Attenuated Type I alveolar cells are particularly susceptible to damage but are not capable of replacing themselves following injury. Repair and routine replacement is carried out by Type II alveolar cells which suspend their secretory activity, divide and differentiate into Type I cells. With chronic injury, Type II cells divide but do not differentiate into Type I cells. As a result, parts of the air spaces become lined by cuboidal Type II cells which reduces the area available for gas exchange.

Type II alveolar cells are responsible for the secretion and turnover of surfactant, a macroaggregate of phospholipids (primarily dipalmitoylphosphatidylcholine) and proteins, which coats the entire alveolar surface. The surfactant reduces the surface tension of water molecules covering the alveolar surface, prevents the collapse of the lung during exhalation, and reduces the amount of energy necessary to reinflate the lung. Growth factors, hormones and simple mechanical stretching stimulate secretion of surfactant. With each inhalation the alveolar surface area may increase as much as 80%, and the secretion of surfactant must cover the expanded area. In order to maintain a thin, surface-active film during exhalation, the excess surfactant is removed by the endocytotic pathways of Type II cells.

About 10% of surfactant is protein, including a family of large, acidic glycoproteins (SP-A) essential to the recycling of surfactant and two smaller hydrophobic peptides (SP-B, SP-C) that promote surfactant spreading. At birth, the maturity of the lungs and adequate surfactant are critical to prevent collapse at first breath. Hyaline membrane disease and respiratory distress syndrome involve inadequate surfactant which may be overcome by administration of glucocorticoids at critical stages of development and/or surfactant replacement at birth.

Fluids do not normally enter the air space because of negative osmotic pressure in the interstitium and diversion of excess fluid into the lymph system. However, if endothelial cells are damaged and excess protein leaks into the interstitium, osmotic pressure changes from negative to positive, the Type I cell layer is damaged, and fluids leak into the alveoli.

An extensive treatment of lung cell biology may be found in Massaro (1989, *Lung Cell Biology*, Marcel Dekker Inc, New York N.Y.), incorporated herein by reference.

Disorders of the Lung

Emphysema is a disorder of the lung characterized by destruction of the walls of the alveoli. Consequent enlargement of the distal airspaces leads to impaired ability of the cardiopulmonary system to deliver oxygen to other organs. Individuals suffering with emphysema typically have difficulty exhaling due to the loss of elastic recoil and airway support normally provided by the alveoli. Moreover, the loss of alveolar tissue diminishes the surface area available for gas exchange and the loss of pulmonary capillaries limits the capacity of the right heart to transfer the cardiac output across the lungs.

Emphysema can result from a common lethal hereditary disorder, α1-antitrypsin (α1-AT) deficiency. Neutrophil elastase which is released by activated or lysed neutrophils, cleaves the major connective tissue components of the alveolar walls, including elastin, collagen types I, III, and IV, laminin, fibronectin, and the protein components of proteoglycans. In normal individuals, neutrophil elastase is inhibited by α1-AT and by secreted leukoprotease inhibitor, a 12 kD protein produced by airway secretory cells. Uninhibited neutrophil elastase also interacts with receptors on the surface of alveolar macrophages which results in their activation. Activated macrophages release leukotriene B4, a potent neutrophil chemoattractant, further increasing the burden of neutrophils and of neutrophil elastase in the lung. The presence of uninhibited neutrophil elastase in the lower respiratory tract causes progressive destruction of the alveolar walls.

Emphysema is common among cigarette smokers. Cigarette smoke induces alveolar macrophages to release chemoattractants for neutrophils and causes the release of free radicals, such as superoxide and hydrogen peroxide, which oxidize the Met 358 residue of α1-AT, inactivates α1-AT and results in alveolar damage.

Bronchitis

Bronchitis is a disorder characterized by inflammation of the airway epithelium, generally involving both large and small airways. The inflammation causes mucous hypersecretion, leading to dysfunction of host defenses and bacterial colonization of the retained secretions and infections. In some individuals, the inflammation is sufficiently extensive that it is characterized by progressive derangement of the airway architecture, loss of lung function, and respiratory limitation.

The most aggressive form of bronchitis is cystic fibrosis (CF), which is caused by a mutation of the CF transmembrane regulator (CFTR). Affected individuals develop frequent respiratory infections localized to the epithelial surface of the airways. Eventually those affected by CF develop the chronic production of thick, sticky sputum which, in turn, is colonized with bacteria. Thus CF is characterized by chronic inflammation and infection of the airways, and progressive deterioration of airway function, derangement of pulmonary parenchyma, and finally respiratory failure. In individuals suffering with CF, the inflammation on the airway epithelial surface is so intense that both α1-AT and leukoprotease inhibitor defenses are overwhelmed and rendered ineffective. Moreover, there are decreased levels of glutathione, an antioxidant, in the fluid covering the respiratory epithelial surface. As a result the epithelium develops chronic, oxidant-induced damage.

The most common form of bronchitis is that associated with cigarette smoking. It has features similar to those of the bronchitis observed in CF, although in a milder form. The inflammatory population includes neutrophils and alveolar macrophages which release an increased burden of oxidants and proteases, including neutrophil elastase, on the airway epithelial surface.

Mechanisms of respiratory tissue injury from cigarette smoking are reviewed in McCusker (1992) Amer J Med 93S:18–21, and inflammatory lung diseases are reviewed in Jennings and Crystal (In: Gallin et al. (1992) *Inflammation: Basic Principles and Clinical Correlates*, Raven Press, New York N.Y.).

Pulmonary Fibrosis

In pulmonary fibrosis, alveolar walls are thickened by scarring of the interstitium as a result of inflammatory disorders of the lower respiratory tract. Pulmonary fibrosis increases the work required for inspiration and reduces the surface area of the pulmonary capillary bed; transfer of oxygen to the pulmonary capillaries and other organs is limited. Alveolar macrophages, neutrophils, lymphocytes, and eosinophils dominate to variable degrees in different disorders.

The proliferation and function of lung fibroblasts can be directly stimulated or inhibited by a variety of substances that cause lung damage which can eventually lead to interstitial pulmonary fibrosis. These substances include mineral particulates such as silica and asbestos, the metal beryllium, and the antineoplastic drug bleomycin. Idiopathic pulmonary fibrosis (IPF) is a form of pulmonary fibrosis which may result from alveolar inflammation initiated by IgG immune complexes (Jennings and Crystal, supra).

Asbestos exposure, for example, results in lung lesions extending along the alveolar and duct walls that are characterized by a diffuse thickening of the tissue due to increased deposition of connective tissue components. Early lung response to a variety of pneumotoxic agents is characterized by an initial interaction of alveolar and interstitial macrophages with the asbestos fibers leading to complement activation and the production of C5a, a potent chemotactic factor for macrophages and neutrophils, followed by an influx of inflammatory and immune cells, into the exposed tissues.

Asbestosis is characterized by pulmonary cellular hyperplasia, inflammation, and accumulation of connective tissue matrix. Macrophages present at and recruited to the site of asbestosis exposure secrete a number of potent inflammatory mediators and cytokines, including various arachidonic acid metabolites, including prostaglandins and leukotrienes, and bioactive peptides such as platelet-derived growth factor, TGF-β, macrophage-derived growth factor, and IL-1. The resulting proliferation of lung fibroblasts eventually leads to fibrosis.

Interstitial pulmonary fibrosis caused by asbestos exposure is reviewed by Brody (In: Gallin et al. (1992) *Inflammation: Basic Principles and Clinical Correlates*, Raven Press, New York N.Y.).

Asthma

Asthma is characterized by a reversible airways obstruction or inflammation which is attributed to hypersensitivity to stimuli. Symptoms include the wheezing, coughing, and shortness of breath in a mild attack which may progress through three worsening stages all the way to respiratory arrest. Asthma attacks are due to spasm of smooth muscle, edema of the mucosa, increased mucous secretion, eosinophilic infiltration of the mucosa and walls, and injury including desquamation of the epithelium. Both the prevalence and mortality from asthma has increased worldwide.

Typically all asthmatics with active disease have hyperresponsive airways and an exaggerated bronchoconstrictor response to many different stimuli which may include exercise. Mast cells are involved in the response to different inhaled allergens. Eosinophils contribute to the pathogenesis of chronic inflammation by releasing proteins capable of damaging the epithelium. Although the role of neutrophils is unknown, macrophages, lymphocytes and their secretions have been implicated in inflammation. Examples of secreted molecules include histamine, leukotrienes, prostaglandins, platelet activating factor, etc.

Neurogenic/cholinergic factors also influence the bronchorestrictive response. When irritants are inhaled, sensory neurons release substance P, neurokinin A, and calcitonin-related peptide. Etiologic factors, even for allergy-induced asthma, are often difficult to assess, and attacks may be complicated by emotional components such as stress. Nonspecific allergic irritants include cigarette smoke, viral and bacterial infections, pollens, molds, epidermal scales, dust mites, etc.

Drug therapy includes five useful groups—β-adrenergic agents (epinephrine, isoproterenol, terbutaline, albuterol, etc) which relax smooth muscle and inhibit mediator release; theophylline which relaxes smooth muscle and inhibits release of calcium and other chemical mediators; corticosteroids which inhibit leukocytes and leukotriene release; chromolyn sodium which inhibits mediator release and is useful for maintenance therapy; and anticholinergic agents such as atropine which block cholinergic pathways and provide bronchodilation.

These and other respiratory diseases are discussed more fully in *The Merck Manual of Diagnosis and Therapy* (1992) Merck Research Laboratories, Rahway, N.J. and in Seaton et al. (1989) *Crofton and Douglas's Respiratory Diseases*, Blackwell Scientific Publications, Boston.

SUMMARY OF THE INVENTION

The subject invention provides a unique nucleotide sequence which encodes a novel human ICE homolog. The new gene, also known as icel, was first identified in Incyte Clone124985 (SEQ ID NO 1). Incyte Clones194094 (SEQ ID NO 2) and 239 (SEQ ID NO 3) also contain partial icel sequence. The assembled nucleotide sequence presented herein encodes an ICEL polypeptide and represents a new human cysteine protease.

The invention also comprises diagnostic tests for conditions including cancers, disorders or diseases associated with altered icel expression and testing a biological sample with icel oligomers or antibodies to the purified protein.

Further aspects of the invention include an antisense of icel or its control sequences; an expression vector containing icel; host cells or organisms transformed with the expression vector; a method for the production and recovery of ICEL polypeptide from host cells.

The invention further comprises purified ICEL polypeptide; antibodies and inhibitors with specific binding to ICEL; and pharmaceutical compositions containing the peptide, antibodies or inhibitors for treatment of conditions associated with altered ICEL expression.

DESCRIPTION OF THE FIGURES

FIGS. 1A and 1B display the nucleotide and amino acid sequences for icel.

FIGS. 2A and 2B show the amino acid alignment of ICEL with a human cysteine protease. Alignments shown were produced using the multisequence alignment program of DNASTAR software (DNASTAR Inc, Madison Wis.).

DETAILED DESCRIPTION OF THE INVENTION

Definitions

Figure 3:
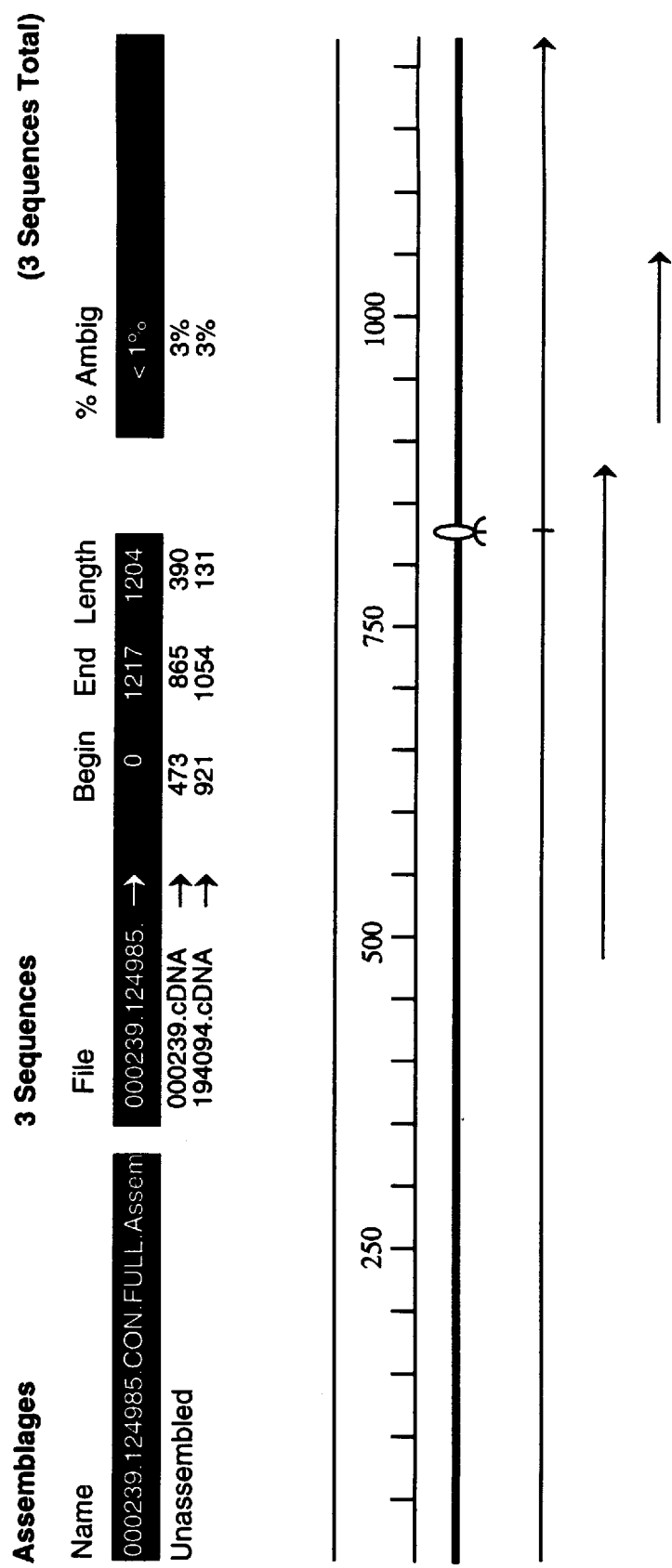
FIG. 3 provides the consensus sequence for icel as printed from the computer screen. The exact alignments and positions of overlap among the three Incyte clones are shown in tabular and schematic form.

As used herein, the abbreviation for the ICE homolog in lower case (icel) refers to a gene, cDNA, RNA or nucleic acid sequence while the upper case version (ICEL) refers to a protein, polypeptide, peptide, oligopeptide, or amino acid sequence.

An "oligonucleotide" or "oligomer" is a stretch of nucleotide residues which has a sufficient number of bases to be used in a polymerase chain reaction (PCR). These short sequences are based on (or designed from) genomic or cDNA sequences and are used to amplify, confirm, or reveal the presence of an identical, similar or complementary DNA or RNA in a particular cell or tissue. Oligonucleotides or oligomers comprise portions of a DNA sequence having at least about 10 nucleotides and as many as about 50 nucleotides, preferably about 15 to 30 nucleotides. They are chemically synthesized and may be used as probes.

"Probes" are nucleic acid sequences of variable length, preferably between at least about 10 and as many as about 6,000 nucleotides, depending on use. They are used in the detection of identical, similar, or complementary nucleic acid sequences. Longer length probes are usually obtained from a natural or recombinant source, are highly specific and much slower to hybridize than oligomers. They may be single- or double-stranded and are carefully designed to have specificity in PCR, hybridization membrane-based, or ELISA-like technologies.

"Reporter" molecules are chemical moieties used for labelling a nucleic or amino acid sequence. They include, but are not limited to, radionuclides, enzymes, fluorescent, chemi-luminescent, or chromogenic agents. Reporter molecules associate with, establish the presence of, and may allow quantification of a particular nucleic or amino acid sequence.

A "portion" or "fragment" of a polynucleotide or nucleic acid comprises all or any part of the nucleotide sequence having fewer nucleotides than about 6 kb, preferably fewer than about 1 kb which can be used as a probe. Such probes may be labelled with reporter molecules using nick translation, Klenow fill-in reaction, PCR or other methods well known in the art. After pretesting to optimize reaction conditions and to eliminate false positives, nucleic acid probes may be used in Southern, northern or in situ hybridizations to determine whether DNA or RNA encoding the protein is present in a biological sample, cell type, tissue, organ or organism.

"Recombinant nucleotide variants" are polynucleotides which encode a protein. They may be synthesized by making use of the "redundancy" in the genetic code. Various codon substitutions, such as the silent changes which produce specific restriction sites or codon usage-specific mutations, may be introduced to optimize cloning into a plasmid or viral vector or expression in a particular prokaryotic or eukaryotic host system, respectively.

"Linkers" are synthesized palindromic nucleotide sequences which create internal restriction endonuclease sites for ease of cloning the genetic material of choice into various vectors. "Polylinkers" are engineered to include multiple restriction enzyme sites and provide for the use of both those enzymes which leave 5' and 3' overhangs such as BamHI, EcoRI, PstI, KpnI and Hind III or which provide a blunt end such as EcoRV, SnaBI and StuI.

"Control elements" or "regulatory sequences" are those nontranslated regions of the gene or DNA such as enhancers, promoters, introns and 3' untranslated regions which interact with cellular proteins to carry out replication, transcription, and translation. They may occur as boundary sequences or even split the gene. They function at the molecular level and along with regulatory genes are very important in development, growth, differentiation and aging processes.

"Chimeric" molecules are polynucleotides or polypeptides which are created by combining one or more of nucleotide sequences of this invention (or their parts) with additional nucleic acid sequence(s). Such combined sequences may be introduced into an appropriate vector and expressed to give rise to a chimeric polypeptide which may be expected to be different from the native molecule in one or more of the following characteristics: cellular location, distribution, ligand-binding affinities, interchain affinities, degradation/turnover rate, signalling, etc.

"Active" is that state which is capable of being useful or of carrying out some role. It specifically refers to those forms, fragments, or domains of an amino acid sequence which display the biologic and/or immunogenic activity characteristic of the naturally occurring peptide.

"Naturally occurring ICEL" refers to a polypeptide produced by cells which have not been genetically engineered or which have been genetically engineered to produce the same sequence as that naturally produced. Specifically contemplated are various polypeptides which arise from post-translational modifications. Such modifications of the polypeptide include but are not limited to acetylation, carboxylation, glycosylation, phosphorylation, lipidation and acylation.

"Derivative" refers to those polypeptides which have been chemically modified by such techniques as ubiquitination, labelling (see above), pegylation (derivatization with poly-ethylene glycol), and chemical insertion or substitution of amino acids such as ornithine which do not normally occur in human proteins.

"Recombinant polypeptide variant" refers to any polypeptide which differs from naturally occurring ICEL by amino acid insertions, deletions and/or substitutions, created using recombinant DNA techniques. Guidance in determining which amino acid residues may be replaced, added or deleted without abolishing characteristics of interest may be found by comparing the sequence of ICEL with that of related polypeptides and minimizing the number of amino acid sequence changes made in highly conserved regions.

Amino acid "substitutions" are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid "insertions" or "deletions" are changes to or within an amino acid sequence. They typically fall in the range of about 1 to 5 amino acids. The variation allowed in a particular amino acid sequence may be experimentally determined by producing the peptide synthetically or by systematically making insertions, deletions, or substitutions of nucleotides in the icel sequence using recombinant DNA techniques.

A "signal or leader sequence" is a short amino acid sequence which or can be used, when desired, to direct the polypeptide through a membrane of a cell. Such a sequence may be naturally present on the polypeptides of the present invention or provided from heterologous sources by recombinant DNA techniques.

An "oligopeptide" is a short stretch of amino acid residues and may be expressed from an oligonucleotide. It may be functionally equivalent to and either the same length as or considerably shorter than a "fragment", "portion", or "segment" of a polypeptide. Such sequences comprise a stretch of amino acid residues of at least about 5 amino acids and often about 17 or more amino acids, typically at least about 9 to 13 amino acids, and of sufficient length to display biologic and/or immunogenic activity.

An "inhibitor" is a substance which retards or prevents a chemical or physiological reaction or response. Common inhibitors include but are not limited to antisense molecules, antibodies, antagonists and their derivatives.

A "standard" is a quantitative or qualitative measurement for comparison. Preferably, it is based on a statistically appropriate number of samples and is created to use as a basis of comparison when performing diagnostic assays, running clinical trials, or following patient treatment profiles. The samples of a particular standard may be normal or similarly abnormal.

"Animal," as used herein, may be defined to include human, domestic (cats, dogs, etc), agricultural (cows, horses, sheep, goats, chicken, fish, etc) or test species (frogs, mice, rats, rabbits, simians, etc).

"Conditions" includes cancers, disorders or diseases in which ICEL activity has been implicated. These specifically include, but are not limited to, asthma, bronchitis, cachexia, emphysema, rheumatoid arthritis, pulmonary fibrosis, septic shock, inflammatory bowel disease and insulin-dependent diabetes mellitus.

Since the list of technical and scientific terms cannot be all encompassing, any undefined terms shall be construed to have the same meaning as is commonly understood by one of skill in the art to which this invention belongs. Furthermore, the singular forms "a", "an" and "the" include plural referents unless the context clearly dictates otherwise. For example, reference to a "restriction enzyme" or a "high fidelity enzyme" may include mixtures of such enzymes and any other enzymes fitting the stated criteria, or reference to the method includes reference to one or more methods for obtaining cDNA sequences which will be known to those skilled in the art or will become known to them upon reading this specification.

Before the present sequences, variants, formulations and methods for making and using the invention are described, it is to be understood that the invention is not to be limited only to the particular sequences, variants, formulations or methods described. The sequences, variants, formulations and methodologies may vary, and the terminology used herein is for the purpose of describing particular embodiments. The terminology and definitions are not intended to be limiting since the scope of protection will ultimately depend upon the claims.

DESCRIPTION OF THE INVENTION

The present invention provides for purified polynucleotide which encodes an ICE homolog which was expressed in human lung tissue and isolated therefrom. The sequence was identified by its similarity to human cysteine protease.

Purified ICE nucleotide sequences have numerous applications in techniques known to those skilled in the art of molecular biology. These techniques include their use as PCR or hybridization probes, for chromosome and gene mapping, in the production of sense or antisense nucleic acids, in screening for new therapeutic molecules, etc. These examples are well known and are not intended to be limiting. Furthermore, the nucleotide sequences disclosed herein may be used in molecular biology techniques that have not yet been developed, provided the new techniques rely on properties of nucleotide sequences that are currently known, including but not limited to such properties as the triplet genetic code and specific base pair interactions.

As a result of the degeneracy of the genetic code, a multitude of ICEL-encoding nucleotide sequences may be produced and some of these will bear only minimal homology to the endogenous sequence of any known and naturally occurring ICE sequence. This invention has specifically contemplated each and every possible variation of nucleotide sequence that could be made by selecting combinations based on possible codon choices. These combinations are made in accordance with the standard triplet genetic code as applied to the nucleotide sequence of naturally occurring ICEL and all such variations are to be considered as being specifically disclosed.

Although the icel nucleotide sequence and its derivatives or variants are preferably capable of identifying the nucleotide sequence of the naturally occurring ICEL under optimized conditions, it may be advantageous to produce ICEL-encoding nucleotide sequences possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding the ICEL without altering the encoded amino acid sequence include the production of RNA transcripts having more desirable properties, such as a longer half-life, than transcripts produced from the naturally occurring sequence.

Nucleotide sequences encoding ICEL may be joined to a variety of other nucleotide sequences by means of well established recombinant DNA techniques (Sambrook J et al (1989) *Molecular Cloning: A Laboratory Manual*, Cold Spring Harbor Laboratory, Cold Spring Harbor N.Y.; or Ausubel FM et al (1989) *Current Protocols in Molecular Biology*, John Wiley & Sons, New York City). Useful sequences for joining to icel include an assortment of cloning vectors such as plasmids, cosmids, lambda phage derivatives, phagemids, and the like. Vectors of interest include vectors for replication, expression, probe generation, sequencing, and the like. In general, vectors of interest may contain an origin of replication functional in at least one organism, convenient restriction endonuclease sensitive sites, and selectable markers for one or more host cell systems.

PCR, as described in U.S. Pat. Nos. 4,683,195; 4,800,195; and 4,965,188, provides additional uses for oligonucleotides based upon the icel nucleotide sequence. Such oligomers are generally chemically synthesized, but they may be of recombinant origin or a mixture of both. Oligomers generally comprise two nucleotide sequences, one with sense orientation (5'->3') and one with antisense (3' to 5') employed under optimized conditions for identification of a specific gene or diagnostic use. The same two oligomers, nested sets of oligomers, or even a degenerate pool of oligomers may be employed under less stringent conditions for identification and/or quantitation of closely related DNA or RNA sequences.

Full length genes may be cloned utilizing partial nucleotide sequence and various methods known in the art. Gobinda et al (1993; PCR Methods Applic 2:318–22) disclose "restriction-site PCR" as a direct method which uses universal primers to retrieve unknown sequence adjacent to a known locus. First, genomic DNA is amplified in the presence of primer to linker and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase. Gobinda et al present data concerning Factor IX for which they identified a conserved stretch of 20 nucleotides in the 3' noncoding region of the gene.

Inverse PCR is the first method to report successful acquisition of unknown sequences starting with primers based on a known region (Triglia T et al(1988) Nucleic Acids Res 16:8186). The method uses several restriction enzymes to generate a suitable fragment in the known region of a gene. The fragment is then circularized by intramolecular ligation and used as a PCR template. Divergent primers are designed from the known region. The multiple rounds of restriction enzyme digestions and ligations that are necessary prior to PCR make the procedure slow and expensive (Gobinda et al, supra).

Capture PCR (Lagerstrom M et al (1991) PCR Methods Applic 1:111–19) is a method for PCR amplification of DNA fragments adjacent to a known sequence in human and YAC DNA. As noted by Gobinda et al (supra), capture PCR also requires multiple restriction enzyme digestions and ligations to place an engineered double-stranded sequence into an unknown portion of the DNA molecule before PCR. Although the restriction and ligation reactions are carried out simultaneously, the requirements for extension, immobilization and two rounds of PCR and purification prior to sequencing render the method cumbersome and time consuming.

Parker J D et al (1991; Nucleic Acids Res 19:3055–60), teach walking PCR, a method for targeted gene walking which permits retrieval of unknown sequence. In this same vein, PromoterFinder™ a new kit available from Clontech (Palo Alto Calif.) uses PCR and primers derived from p53 to walk in genomic DNA. Nested primers and special PromoterFinder libraries are used to detect upstream sequences such as promoters and regulatory elements. This process avoids the need to screen libraries and is useful in finding intron/exon junctions.

Another new PCR method, "Improved Method for Obtaining Full Length cDNA Sequences" by Guegler et al, patent application Ser. No 08/487,112, filed Jun. 7, 1995 and hereby incorporated by reference, employs XL-PCR™ (Perkin-Elmer, Foster City Calif.) to amplify and extend partial nucleotide sequence into longer pieces of DNA. This method was developed to allow a single researcher to process multiple genes (up to 20 or more) at one time and to obtain an extended (possibly full-length) sequence within 6–10 days. This new method replaces methods which use labelled probes to screen plasmid libraries and allow one researcher to process only about 3–5 genes in 14–40 days.

In the first step, which can be performed in about two days, any two of a plurality of primers are designed and synthesized based on a known partial sequence. In step 2, which takes about six to eight hours, the sequence is extendedly PCR amplification of a selected library. Steps 3 and 4, which take about one day, are purification of the amplified cDNA and its ligation into an appropriate vector. Step 5, which takes about one day, involves transforming and growing up host bacteria. In step 6, which takes approximately five hours, PCR is used to screen bacterial clones for extended sequence. The final steps, which take about one day, involve the preparation and sequencing of selected clones.

If the full length cDNA has not been obtained, the entire procedure is repeated using either the original library or some other preferred library. The preferred library may be one that has been size-selected to include only larger cDNAs or may consist of single or combined commercially available libraries, eg. lung, liver, heart and brain from Gibco/BRL (Gaithersburg Md.). The cDNA library may have been prepared with oligo (dT) or random priming. Random primed libraries are preferred in that they will contain more sequences which contain 5' ends of genes. A randomly primed library may be particularly useful if an oligo (dT) library does not yield a complete gene. It must be noted that the larger and more complex the protein, the less likely it is that the complete gene will be found in a single plasmid.

A new method for analyzing either the size or the nucleotide sequence of PCR products is capillary electrophoresis. Systems for rapid sequencing are available from Perkin Elmer (Foster City Calif.), Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis provides greater resolution and is many times faster than standard gel based procedures. It is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Another aspect of the subject invention is to provide for icel hybridization probes which are capable of hybridizing with naturally occurring nucleotide sequences encoding ICEL. The stringency of the hybridization conditions will determine whether the probe identifies only the native nucleotide sequence of icel or sequences of other closely related ICE molecules. If degenerate icel nucleotide sequences of the subject invention are used for the detection of related ICE encoding sequences, they should preferably contain at least 50% of the nucleotides of the sequences presented herein. Hybridization probes of the subject invention may be derived from the nucleotide sequences of the SEQ ID NOs 1–3 or from surrounding or included genomic sequences comprising untranslated regions such as promoters, enhancers and introns. Such hybridization probes may be labelled with appropriate reporter molecules.

Means for producing specific hybridization probes for ICE or its homologs include oligolabelling, nick translation, end-labelling or PCR amplification using a labelled nucleotide. Alternatively, the cDNA sequence may be cloned into a vector for the production of mRNA probe. Such vectors are known in the art, are commercially available, and may be used to synthesize RNA probes in vitro by addition of an appropriate RNA polymerase such as T7, T3 or SP6 and labelled nucleotides. A number of companies (such as Pharmacia Biotech, Piscataway N.J.; Promega, Madison Wis.; US Biochemical Corp, Cleveland, Ohio; etc.) supply commercial kits and protocols for these procedures.

It is also possible to produce a DNA sequence, or portions thereof, entirely by synthetic chemistry. Sometimes the source of information for producing this sequence comes from the known homologous sequence from closely related organisms. After synthesis, the nucleic acid sequence can be used alone or joined with a pre-existing sequence and inserted into one of the many available DNA vectors and their respective host cells using techniques well known in the art. Moreover, synthetic chemistry may be used to introduce specific mutations into the nucleotide sequence. Alternatively, a portion of sequence in which a mutation is desired can be synthesized and recombined with a portion of an existing genomic or recombinant sequence.

The icel nucleotide sequences can be used individually in a diagnostic test or assay to detect disorder or disease processes associated with abnormal levels of IL expression. The nucleotide sequence is added to a sample (fluid, cell or tissue) from a patient under hybridizing conditions. After an incubation period, the sample is washed with a compatible fluid which optionally contains a reporter molecule which will bind the specific nucleotide. After the compatible fluid is rinsed off, the reporter molecule is quantitated and compared with a standard for that fluid, cell or tissue. If icel expression is significantly different from the standard, the assay indicates the presence of disorder or disease. The form of such qualitative or quantitative methods may include northern analysis, dot blot or other membrane-based technologies, dip stick, pin or chip technologies, PCR, ELISAs or other multiple sample format technologies.

This same assay, combining a sample with the nucleotide sequence, is applicable in evaluating the efficacy of a particular therapeutic treatment regime. It may be used in animal studies, in clinical trials, or in monitoring the treatment of an individual patient. First, standard expression must be established for use as a basis of comparison. Second, samples from the animals or patients affected by a disorder or disease are combined with the nucleotide sequence to evaluate the deviation from the standard or normal profile. Third, an existing therapeutic agent is administered, and a treatment profile is generated. The assay is evaluated to determine whether the profile progresses toward or returns to the standard pattern. Successive treatment profiles may be used to show the efficacy of treatment over a period of several days or several months.

The nucleotide sequence for icel can also be used to generate probes for mapping the native genomic sequence. The sequence may be mapped to a particular chromosome or to a specific region of the chromosome using well known techniques. These include in situ hybridization to chromosomal spreads (Verma et al (1988) *Human Chromosomes: A Manual of Basic Techniques*, Pergamon Press, New York City), flow-sorted chromosomal preparations, or artificial chromosome constructions such as yeast artificial chromosomes (YACs), bacterial artificial chromosomes (BACs), bacterial P1 constructions or single chromosome cDNA libraries.

In situ hybridization of chromosomal preparations and physical mapping techniques such as linkage analysis using established chromosomal markers are invaluable in extending genetic maps. Examples of genetic maps can be found in Science (1994; 265:1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. between normal and carrier or affected individuals.

The nucleotide sequence encoding ICEL may be used to produce an amino acid sequence using well known methods of recombinant DNA technology Goeddel (1990, *Gene Expression Technology, Methods and Enzymology*, Vol 185, Academic Press, San Diego Calif.) is one among many publications which teach expression of an isolated, purified nucleotide sequence. The amino acid or peptide may be expressed in a variety of host cells, either prokaryotic or eukaryotic. Host cells may be from the same species from which the nucleotide sequence was derived or from a different species. Advantages of producing an amino acid sequence or peptide by recombinant DNA technology include obtaining adequate amounts for purification and the availability of simplified purification procedures.

Cells transformed with icel nucleotide sequence may be cultured under conditions suitable for the expression and recovery of peptide from cell culture. The peptide produced by a recombinant cell may be secreted or may be contained intracellularly depending on the sequence and/or the vector used. In general, it is more convenient to prepare recombinant proteins in secreted form, and this is accomplished by ligating icel to a recombinant nucleotide sequence which directs its movement through a particular prokaryotic or eukaryotic cell membrane. Other recombinant constructions may join icel to nucleotide sequence encoding a polypeptide domain which will facilitate protein purification (Kroll D J et al (1993) DNA Cell Biol 12:441–53).

Direct peptide synthesis using solid-phase techniques (Stewart et al (1969) *Solid-Phase Peptide Synthesis*, W H Freeman Co, San Francisco Calif.; Merrifield J (1963) J Am Chem Soc 85:2149–2154) is an alternative to recombinant or chimeric peptide production. Automated synthesis may be achieved, for example, using Applied Biosystems 431A Peptide Synthesizer in accordance with the instructions provided by the manufacturer. Additionally ICEL or any part thereof may be mutated during direct synthesis and combined using chemical methods with other ICE sequences or any part thereof. This chimeric nucleotide sequence can also be placed in an appropriate vector and host cell to produce a variant peptide.

Although an amino acid sequence or oligopeptide used for antibody induction does not require biological activity, it must be immunogenic. ICEL used to induce specific antibodies may have an amino acid sequence consisting of at least five amino acids and preferably at least 10 amino acids. Short stretches of amino acid sequence may be fused with those of another protein such as keyhole limpet hemocyanin, and the chimeric peptide used for antibody production. Alternatively, the peptide may be of sufficient length to contain an entire domain.

Antibodies specific for ICEL may be produced by inoculation of an appropriate animal with an antigenic fragment of the peptide. An antibody is specific for ICEL if it is produced against an epitope of the polypeptide and binds to at least part of the natural or recombinant protein. Antibody production includes not only the stimulation of an immune response by injection into animals, but also analogous processes such as the production of synthetic antibodies, the screening of recombinant immunoglobulin libraries for specific-binding molecules (Orlandi R et al (1989) PNAS 86:3833–3837, or Huse W D et al (1989) Science 256:1275–1281), or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules which specifically bind ICEL. Antibodies or other appropriate molecules generated against a specific immunogenic peptide fragment or oligopeptide can be used in Western analysis, enzyme-linked immunosorbent assays (ELISA) or similar tests to establish the presence of or to quantitate amounts of ICEL active in normal, diseased, or therapeutically treated cells or tissues.

The examples below are provided to illustrate the subject invention. These examples are provided by way of illustration and are not included for the purpose of limiting the invention.

EXAMPLES

I cDNA Library Construction

The icel sequence of this application (SEQ ID No 1; FIG. 1) was first identified among the sequences comprising the lung cDNA library. Stratagene (La Jolla Calif.) used normal lung tissue from a 72 year old Caucasian male (Catalog #937210) and oligo (dT) priming to make this cDNA library. Synthetic adapter oligonucleotides were ligated onto the cDNA molecules enabling them to be inserted into the Uni-ZAP™ vector system (Stratagene). This allowed high efficiency unidirectional (sense orientation) lambda library construction and the convenience of a plasmid system with blue/white color selection to detect clones with cDNA insertions.

The quality of the cDNA library was screened using DNA probes, and then, the pBluescript® phagemids (Stratagene) were excised en masse from the library. This phagemid allows the use of a plasmid system for easy insert characterization, sequencing, site-directed mutagenesis, the creation of unidirectional deletions and expression of fusion polypeptides. Subsequently, the custom-constructed library phage particles were infected into E. coli host strain XL1-Blue® (Stratagene). The high transformation efficiency of this bacterial strain increases the probability that the cDNA library will contain rare, under-represented clones. Alternative unidirectional vectors might include, but are not limited to, pcDNAI (Invitrogen, San Diego Calif.) and pSHlox-1 (Novagen, Madison Wis.).

II Isolation of cDNA Clones

The phagemid forms of individual cDNA clones were obtained by the in vivo excision process, in which the host bacterial strain was co-infected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the pBluescript phagemid and the cDNA insert. The phagemid DNA was released from the cells and purified, and used to reinfect fresh host cells (SOLR, Stratagene) where double-stranded phagemid DNA was produced. Because the phagemid carries the gene for β-lactamase, the newly transformed bacteria were selected on medium containing ampicillin.

Phagemid DNA was also purified using the QIAWELL-8 Plasmid Purification System from QIAGEN Inc (Chatsworth Calif.). This product provides a convenient, rapid and reliable high-throughput method for lysing the bacterial cells and isolating highly purified phagemid DNA using QIAGEN anion-exchange resin particles with EMPORE™ membrane technology from 3M (Minneapolis Minn.) in a multiwell format. The DNA was eluted from the purification resin and prepared for DNA sequencing and other analytical manipulations.

In the alternative, DNAs can be purified using Miniprep Kits (Catalog # 77468; Advanced Genetic Technologies Corporation, Gaithersburg Md.). These kits provide a 96-well format and enough reagents for 960 purifications. The recommended protocol supplied with each kit has been employed except for the following changes. First, the 96 wells are each filled with only 1 ml of sterile Terrific broth (LIFE TECHNOLGIES™, Gaithersburg Md.) with carbenicillin at 25 mg/L (2×Carb) and glycerol at 0.4%. After the wells are inoculated, the bacteria are cultured for 24 hours and lysed with 60 μl of lysis buffer. A centrifugation step (Beckman GS-6R @2900 rpm for 5 min) is performed before the contents of the block are added to the primary filter plate. The optional step of adding isopropanol to TRIS buffer is not routinely performed. After the last step in the protocol, samples are transferred to a Beckman 96-well block for storage.

III Sequencing of cDNA Clones

The cDNA inserts from random isolates of the lung library were sequenced in part. Methods for DNA sequencing are well known in the art and employ such enzymes as the Klenow fragment of DNA polymerase I, SEQUENASE® (US Biochemical Corp) or Taq polymerase. Methods to extend the DNA from an oligonucleotide primer annealed to the DNA template of interest have been developed for both single- and double-stranded templates. Chain termination reaction products were separated using electrophoresis and detected via their incorporated, labelled precursors. Recent improvements in mechanized reaction preparation, sequencing and analysis have permitted expansion in the number of sequences that can be determined per day. Preferably, the process is automated with machines such as the Hamilton Micro Lab 2200 (Hamilton, Reno Nev.), Peltier Thermal Cycler (PTC200; M J Research, Watertown Mass.) and the Applied Biosystems Catalyst 800 and 377 and 373 DNA sequencers.

The quality of any particular cDNA library may be determined by performing a pilot scale analysis of the cDNAs and checking for percentages of clones containing vector, lambda or E. coli DNA, mitochondrial or repetitive DNA, and clones with exact or homologous matches to public databases. The number of unique sequences, those having no known match in any available database, are then recorded.

IV Homology Searching of cDNA Clones and Their Deduced Proteins

Each sequence so obtained was compared to sequences in GenBank using a search algorithm developed by Applied Biosystems and incorporated into the INHERIT™ 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, is used to search for local sequence alignments (Altschul S F (1993) J Mol Evol 36:290–300; Altschul, S F et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. While it is useful for matches which do not contain gaps, it is inappropriate for performing motif-style searching. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

All three icel molecules presented in this application were identified based on the criteria above. All three are now known to be homologous to human cysteine protease CPP32 (FIG. 2A and 2B). Although Incyte clone 194094 from kidney was originally thought to be a genomic repetitive DNA element sequence and Incyte clone 239 from U937, a homolog of the cysteine protease, HSU13737, their proper alignment is with ICEL as shown in FIG. 3. Names are also subject to change when additional computer analysis against more recent database information is employed. In other cases, a longer sequence has become available (through assembly of contiguous sequences or extension of an individual clone's sequence) and its review against the known databases has resulted in a name change.

V Extension of cDNAs to Full Length

The Incyte clones presented here can be and were used to design oligonucleotide primers for extension of the cDNAs to full length. Primers are designed based on known sequence; one primer is synthesized to initiate extension in the antisense direction (XLR) and the other to extend sequence in the sense direction (XLF). The primers allow the sequence to be extended "outward" generating amplicons containing new, unknown nucleotide sequence for the gene of interest. The primers may be designed using Oligo 4.0 (National Biosciences Inc, Plymouth Minn.), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations was avoided.

The stomach cDNA library was used as a template, and XLR=CAT GAG GAA GTC AGC TCC AGC AG and XLF=TGA ACG GCT CAT GGT ACA TTC AA primers were used to extend and amplify the 124984 sequence. By following the instructions for the XL-PCR kit and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M J Research, Watertown Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

At the end of 28 cycles, 50 µl of the reaction mix was removed; and the remaining reaction mix was run for an additional 10 cycles as outlined below:

Step 1 94° C. for 15 sec
Step 2 65° C. for 1 min
Step 3 68° C. for (10 min+15 sec)/cycle
Step 4 Repeat step 1–3 for 9 additional cycles
Step 5 72° C. for 10 min A 5–10 µl aliquot of the reaction mixture is analyzed by electrophoresis on a low concentration (about 0.6–0.8%) agarose mini-gel to determine which reactions were successful in extending the sequence. Although all extensions potentially contain a full length gene, some of the largest products or bands are selected and cut out of the gel. Further purification involves using a commercial gel extraction method such as QIAQuick™ (QIAGEN Inc). After recovery of the DNA, Klenow enzyme is used to trim single-stranded, nucleotide overhangs creating blunt ends which facilitate religation and cloning.

After ethanol precipitation, the products are redissolved in 13 µl of ligation buffer. Then, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2×Carb. The following day, 12 colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 15 μl of concentrated PCR reaction mix (3.3x) containing 0.75 units of Taq polymerase, a vector primer and one or both of the gene specific primers used for the extension reaction are added to each well. Amplification is performed using the following conditions:
Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid and sequenced.

VI Diagnostic Assay Using ICEL Specific Oligomers

In those cases where a specific condition (see definitions supra) is suspected to involve altered quantities of icel, oligomers may be designed to establish the presence and/or quantity of mRNA expressed in a biological sample. There are several methods currently being used to quantitate the expression of a particular-molecule. Most of these methods use radiolabelled (Melby PC et al 1993 J Immunol Methods 159:235–44) or biotinylated (Duplaa C et al 1993 Anal Biochem 229–36) nucleotides, coamplification of a control nucleic acid, and standard curves onto which the experimental results are interpolated. Quantitation may be speeded up by running the assay in an ELISA format where the oligomer-of-interest is presented in various dilutions and a colorimetric response gives rapid quantitation. For example, ICEL deficiency may result in an abundance of the proinflammatory interleukin molecules, much swelling and discomfort. In like manner, overexpression may cause apoptosis and major tissue damage. In either case, a quick diagnosis may allow health professionals to treat the condition and prevent worsening of the condition. This same assay can be used to monitor progress of the patient as his/her physiological situation moves toward the normal range during therapy.

VII Sense or Antisense Molecules

Knowledge of the correct cDNA sequence of ice or its regulatory elements enable its use as a tool in sense (Youssoufian H and H F Lodish 1993) Mol Cell Biol 13:98–104) or antisense (Eguchi et al (1991) Annu Rev Biochem 60:631–652) technologies for the investigation of gene function. Oligonucleotides, from genomic or cDNAs, comprising either the sense or the antisense strand of the cDNA sequence can be used in vitro or in vivo to inhibit expression. Such technology is now well known in the art, and oligonucleotides or other fragments can be designed from various locations along the sequence.

The gene of interest can be turned off in the short term by transfecting a cell or tissue with expression vectors which will flood the cell with sense or antisense sequences until all copies of the vector are disabled by endogenous nucleases. Stable transfection of appropriate germ line cells or preferably a zygote with a vector containing the fragment will produce a transgenic organism (U.S. Pat. No. 4,736,866, Apr. 12, 1988), which produces enough copies of the sense or antisense sequence to significantly compromise or entirely eliminate normal activity of the icel gene. Frequently, the function of the gene can be ascertained by observing behaviors such as lethality, loss of a physiological pathway, changes in morphology, etc. at the intracellular, cellular, tissue or organismal level.

In addition to using fragments constructed to interrupt transcription of the open reading frame, modifications of gene expression can be obtained by designing antisense sequences to promoters, enhancers, introns, or even to trans-acting regulatory genes. Similarly, inhibition can be achieved using Hogeboom base-pairing methodology, also known as "triple helix" base pairing.

VIII Expression of ICEL

Expression of the ICEL may be accomplished by subcloning the cDNAs into appropriate vectors and transfecting the vectors into host cells. In this case, the cloning vector previously used for the generation of the tissue library also provides for direct expression of the icel sequence in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods will produce a fusion protein corresponding to the first seven residues of β-galactosidase, about 5 to 15 residues which correspond to linker, and the peptide encoded within the icel cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

The cDNA can be shuttled into other vectors known to be useful for expression of protein in specific hosts. Oligonucleotide linkers containing cloning sites as well as a stretch of DNA sufficient to hybridize to the end of the target cDNA (25 bases) can be synthesized chemically by standard methods. These primers can then used to amplify the desired gene fragments by PCR. The resulting fragments can be digested with appropriate restriction enzymes under standard conditions and isolated by gel electrophoresis. Alternatively, similar gene fragments can be produced by digestion of the cDNA with appropriate restriction enzymes and filling in the missing gene sequence with chemically synthesized oligonucleotides. Partial nucleotide sequence from more than one ICE homolog can be ligated together and cloned into appropriate vectors to optimize expression.

Suitable expression hosts for such chimeric molecules include but are not limited to mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

If native promoters are not part of the cDNA, other host specific promoters may be specifically combined with the coding region of icel. They include MMTV, SV40, and metallothionine promoters for CHO cells; trp, lac, tac and T7 promoters for bacterial hosts; and alpha factor, alcohol oxidase and PGH promoters for yeast. In addition, transcription enhancers, such as the rous sarcoma virus (RSV) enhancer, may be used in mammalian host cells. Once homogeneous cultures of recombinant cells are obtained through standard culture methods, large quantities of recombinantly produced peptide can be recovered from the conditioned medium and analyzed using methods known in the art.

IX Isolation of Recombinant ICEL

ICEL may be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen) between the purification domain and the icel sequence may be useful to facilitate expression of ICEL.

X Identification of or Production of ICEL Specific Antibodies

Purified ICEL is used to screen a pre-existing antibody library or to raise antibodies using either polyclonal or monoclonal methodology. In a polyclonal approach, denatured protein from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

Figure 4:
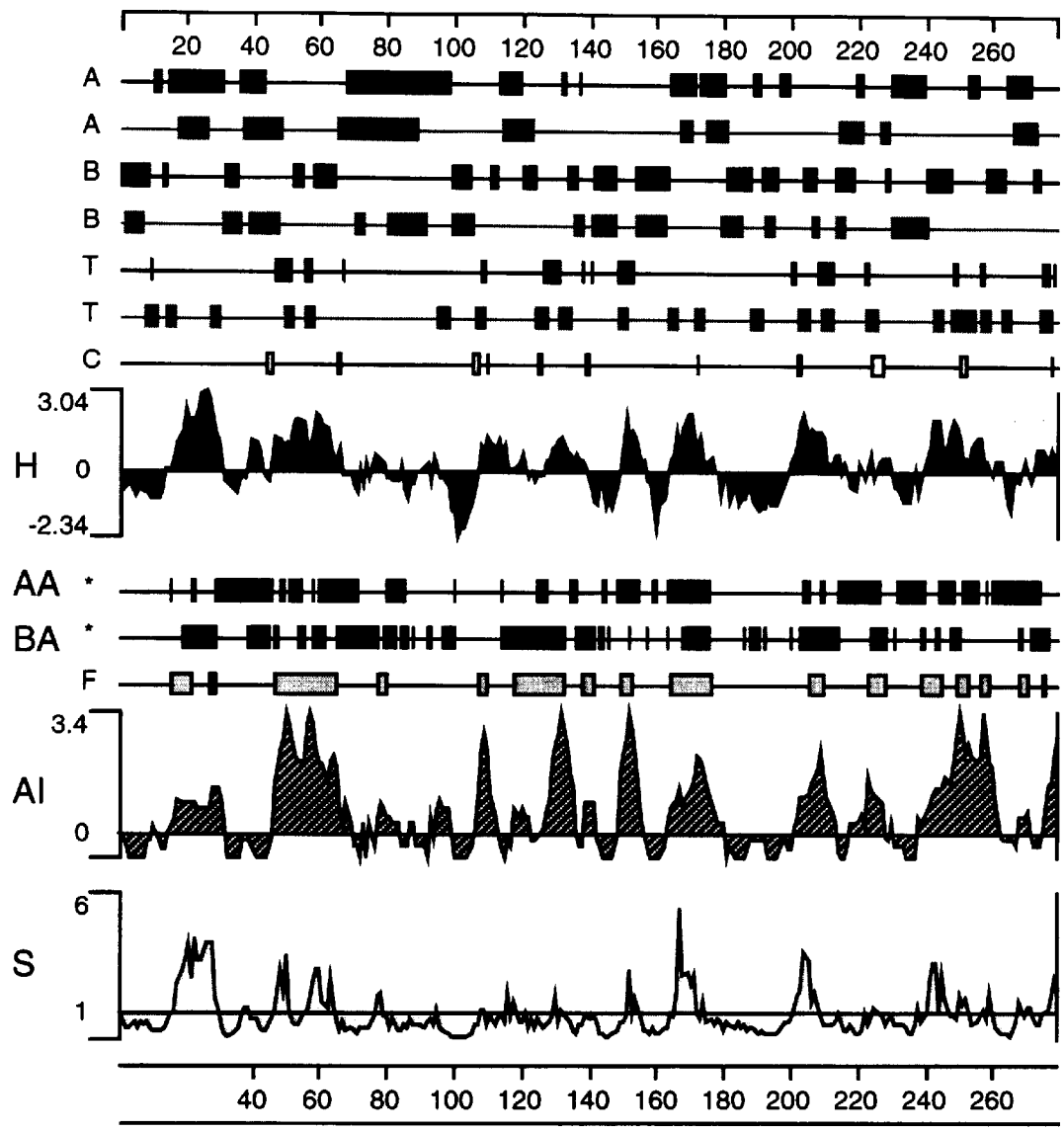
FIG. 4 displays the DNASTAR analysis of ICEL α regions (A), β regions (B), turn regions (T), coil regions (C), hydrophilicity plot (H), a amphipathic regions (AA), β amphipathic regions (BA), antigenic index (AI) and surface probability plot (S) based on the predicted acid amino sequence and composition.

In a monoclonal approach, the amino acid sequence of ICEL, as deduced from translation of the cDNA, is analyzed to determine regions of high immunogenicity. Oligopeptides comprising appropriate hydrophilic regions, as shown in FIG. 4, are synthesized and used in suitable immunization protocols to raise antibodies. Analysis to select appropriate epitopes is described by Ausubel FM et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl- N-hydroxysuccinimide ester (MBS; Ausubel FM et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled ICEL to identify those fusions producing the monoclonal antibody with the desired specificity. In a typical protocol, wells of plates (FAST; Becton-Dickinson, Palo Alto, Calif.) are coated with affinity purified, specific rabbit-anti-mouse antibodies (or suitable anti-species Ig) at 10 mg/ml. The coated wells are blocked with 1% BSA, washed and exposed to supernatants from hybridomas. After incubation the wells are exposed to labeled ICEL, 1 mg/ml. Clones producing antibodies will bind a quantity of labeled ICEL which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least $10^8$/M, preferably $10^9$ to $10^{10}$ or stronger, will typically be made by standard procedures as described in Harlow and Lane (1988) *Antibodies: A Laboratory Manual*, Cold Spring Harbor Laboratory, Cold Spring Harbor N.Y.; and in Goding (1986) *Monoclonal Antibodies: Principles and Practice*, Academic Press, New York City, both incorporated herein by reference.

XI Diagnostic Test Using ICEL Specific Antibodies

Particular ICEL antibodies are useful for the diagnosis of prepathologic conditions, and chronic or acute diseases which are characterized by differences in the amount or distribution of ICEL. To date, ICEL has been found in the U937, kidney, and lung libraries where it is predominantly associated with abnormalities or pathologies which activate monocytes.

Diagnostic tests for ICEL include methods utilizing the antibody and a label to detect ICEL in human body fluids, tissues or extracts of such tissues. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable reporter molecules or labels include those radionuclides, enzymes, fluorescent, chemi-luminescent, or chromogenic agents previously mentioned as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immuno-globulins may be produced as shown in U.S. Pat. No. 4,816,567, incorporated herein by reference.

A variety of protocols for measuring soluble or membrane-bound ICEL, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on ICEL is preferred, but a competitive binding assay may be employed. These assays are described, among other places, in Maddox, Del. et al (1983, J Exp Med 158:1211).

XII Purification of Native ICEL Using Specific Antibodies

Native or recombinant ICEL can be purified by immunoaffinity chromatography using antibodies specific for that particular ICEL. In general, an immunoaffinity column is constructed by covalently coupling the anti-ICEL antibody to an activated chromatographic resin.

Polyclonal immunoglobulins are prepared from immune sera either by precipitation with ammonium sulfate or by purification on immobilized Protein A (Pharmacia Biotech). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia Biotech). The antibody is coupled to the resin, the resin is blocked, and the derivative resin is washed according to the manufacturer's instructions.

Such immunoaffinity columns may be utilized in the purification of ICEL by preparing a fraction from cells containing ICEL in a soluble form. This preparation may be derived by solubilization of whole cells or of a subcellular fraction obtained via differential centrifugation (with or without addition of detergent) or by other methods well known in the art. Alternatively, soluble ICEL containing a signal sequence may be secreted in useful quantity into the medium in which the cells are grown.

A soluble ICEL-containing preparation is passed over the immunoaffinity column, and the column is washed under conditions that allow the preferential absorbance of ICEL (eg, high ionic strength buffers in the presence of detergent). Then, the column is eluted under conditions that disrupt antibody/ICEL binding (eg, a buffer of pH 2–3 or a high concentration of a chaotrope such as urea or thiocyanate ion), and ICEL is collected.

XIII Drug Screening

This invention is particularly useful for screening therapeutic compounds by using binding fragments of ICEL in any of a variety of drug screening techniques. The peptide fragment employed in such a test may either be free in solution, affixed to a solid support, borne on a cell surface or located intracellularly. One may measure, for example, the formation of complexes between ICEL and the agent being tested. Alternatively, one can examine the diminution in complex formation between ICEL and a receptor caused by the agent being tested.

Methods of screening for drugs or any other agents which can affect macrophage activation comprise contacting such an agent with ICEL fragment and assaying for the presence of a complex between the agent and the ICEL fragment. In such assays, the ICEL fragment is typically labelled. After suitable incubation, free ICEL fragment is separated from that present in bound form, and the amount of free or uncomplexed label is a measure of the ability of the particular agent to bind to ICEL.

Another technique for drug screening provides high throughput screening for compounds having suitable binding affinity to the ICEL polypeptides and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with ICEL fragment and washed. Bound ICEL fragment is then detected by methods well known in the art. Purified ICEL can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding ICEL specifically compete with a test compound for binding to ICEL fragments. In this manner, the antibodies can be used to detect the presence of any peptide which shares one or more antigenic determinants with ICEL.

XIV Identification of Molecules Which Interact with ICEL

The inventive purified ICEL is a research tool for identification, characterization and purification of interacting molecules. Appropriate labels are incorporated into ICEL by various methods known in the art and ICEL is used to capture soluble or interact with membrane-bound molecules. A preferred method involves labeling the primary amino groups in ICEL with 125I Bolton-Hunter reagent (Bolton, A E and Hunter, W M (1973) Biochem J 133: 529). This reagent has been used to label various molecules without concomitant loss of biological activity (Hebert C A et al (1991) J Biol Chem 266: 18989–94; McColl S et al (1993) J Immunol 150:4550–4555). Membrane-bound molecules are incubated with the labelled ICEL molecules, washed to removed unbound molecules, and the ICEL complex is quantified. Data obtained using different concentrations of ICEL are used to calculate values for the number, affinity, and association of ICEL.

Labelled ICEL fragments are also useful as a reagent for the purification of molecules with which ICEL interacts, specifically including inhibitors. In one embodiment of affinity purification, ICEL is covalently coupled to a chromatography column. Cells and their membranes are extracted, ICEL is removed and various ICEL-free subcomponents are passed over the column. Molecules bind to the column by virtue of their ICEL affinity. The ICEL-complex is recovered from the column, dissociated and the recovered molecule is subjected to N-terminal protein sequencing or other identification procedure. If the captured molecule has an amino acid sequence, it can be used to design degenerate oligomers for use in cloning the gene from an appropriate cDNA library.

In an alternate method, monoclonal antibodies raised against ICEL fragments are screened to identify those which inhibit the binding of labelled ICEL. These monoclonal antibodies are then used in affinity purification or expression cloning of associated molecules. Other soluble binding molecules are identified in a similar manner. Labelled ICEL is incubated with extracts or other appropriate materials derived from lung, kidney or other tissues with activated monocytes or macrophages. After incubation, ICEL complexes (which are larger than the lone ICEL fragment) are identified by a sizing technique such as size exclusion chromatography or density gradient centrifugation and are purified by methods known in the art. The soluble binding protein(s) are subjected to N-terminal sequencing to obtain information sufficient for database identification, if the soluble protein is known, or for cloning, if the soluble protein is unknown.

XVI Use and Administration of ICEL Peptide, Antibodies or Inhibitors

The peptide ICEL or its antibodies and inhibitors can provide different effects when administered therapeutically.

The peptide is used for the induction of apoptosis in cancerous cells whereas the antibodies and inhibitors are used to lessen or eliminate undue damage caused by macrophages. Each of these molecules or treatments (TSTs) will be formulated in a nontoxic, inert, pharmaceutically acceptable aqueous carrier medium preferably at a pH of about 5 to 8, more preferably 6 to 8, although the pH may vary according to the different characteristics of the peptide, antibody or inhibitor being formulated and the condition to be treated. Characteristics of TSTs include solubility of the molecule, half-life, antigenicity/immunogenicity and the ability of the inhibitor to reach its target(s). These and other characteristics may aid in defining an effective carrier. Native human proteins are preferred as TSTs, but recombinant peptides as well as organic or synthetic molecules resulting from drug screens may be equally effective in particular situations.

TSTs may be delivered by known routes of administration including but not limited to topical creams and gels; transmucosal spray and aerosol; transdermal patch and bandage; injectable, intravenous and lavage formulations; and orally administered liquids and pills particularly formulated to resist stomach acid and enzymes. The particular formulation, exact dosage, and route of administration will be determined by the attending physician and will vary according to each specific situation.

Such determinations are made by considering multiple variables such as the condition to be treated, the TST to be administered, and the pharmacokinetic profile of the particular TST. Additional factors which may be taken into account include disease state (eg. severity) of the patient, age, weight, gender, diet, time and frequency of administration, drug combination, reaction sensitivities, and tolerance/response to therapy. Long acting TST formulations might be administered every 3 to 4 days, every week, or once every two weeks depending on half-life and clearance rate of the particular TST.

Normal dosage amounts may vary from 0.1 to 100,000 micrograms, up to a total dose of about 1 g, depending upon the route of administration. Guidance as to particular dosages and methods of delivery is provided in the literature. (See U.S. Pat. No. 4,657,760; 5,206,344; or 5,225,212.) Those skilled in the art will employ different formulations for different TSTs. Administration to lung cells may necessitate delivery in a manner different from that to kidney or other cells.

It is contemplated that conditions associated with altered ICEL expression are treatable with TSTs. These conditions may be specifically diagnosed by the tests discussed above, and such tests may be used to monitor treatment.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

We claim:

1. An isolated and purified polynucleotide which encodes a human ICE homolog comprising SEQ ID NO:4.

2. A polynucleotide comprising a complement of the polynucleotide of claim 1.

3. A fragment of the polynucleotide of claim 1 comprising SEQ ID NO:2 or SEQ ID NO:3.

4. An isolated and purified nucleotide sequence which is complementary to the fragment of claim 3.

5. A method for detecting a polynucleotide encoding a human ICE homolog in a biological sample containing nucleic acids, the method comprising the steps of:

(a) hybridizing the fragment of claim 4 to at least one of the nucleic acids in the biological sample, thereby forming a hybridization complex; and (b) detecting the hybridization complex, wherein the presence of the hybridization complex correlates with the presence of a polynucleotide encoding human ICE homolog in the biological sample.

6. An expression vector comprising the polynucleotide of claim 1.

7. A host cell transformed with the expression vector of claim 6.

8. A method of producing and purifying a biologically active or immunogenic peptide, the method comprising the steps of:
   a) culturing the host cell of claim 7 under conditions for the expression of the peptide; and
   b) recovering the peptide from the host cell culture.

9. An isolated and purified polynucleotide comprising SEQ ID NO: 1.

* * * * *